US010416090B2

(12) United States Patent
Sacchi et al.

(10) Patent No.: US 10,416,090 B2
(45) Date of Patent: Sep. 17, 2019

(54) SYSTEM AND METHOD FOR THE VIDEO INSPECTION OF A PANTOGRAPH ALONG AN OVERHEAD CONTACT LINE

(71) Applicant: CAMLIN ITALY S.R.L., Parma (IT)

(72) Inventors: Matteo Sacchi, Bagnolo in Piano (IT); Francesco Sciocchetti, Pesaro (IT); Luca Ascari, Parma (IT); Lorenzo Chiesi, Castelnovo Sotto (IT); John Cunningham, Cookstown (IE); Colin McLIroy, Magheralin (IE)

(73) Assignee: CAMLIN ITALY S.R.L., Parma (IT)

( * ) Notice: Subject to any disclaimer, the term of this patent is extended or adjusted under 35 U.S.C. 154(b) by 23 days.

(21) Appl. No.: 15/569,995

(22) PCT Filed: May 9, 2016

(86) PCT No.: PCT/IB2016/052626
§ 371 (c)(1),
(2) Date: Oct. 27, 2017

(87) PCT Pub. No.: WO2016/181280
PCT Pub. Date: Nov. 17, 2016

(65) Prior Publication Data
US 2018/0156737 A1    Jun. 7, 2018

(30) Foreign Application Priority Data

May 12, 2015  (IT) .............................. PR2015A0034

(51) Int. Cl.
*B61K 9/10*     (2006.01)
*G01N 21/95*    (2006.01)
(Continued)

(52) U.S. Cl.
CPC ............... *G01N 21/95* (2013.01); *B60M 1/28* (2013.01); *B61K 9/02* (2013.01); *B61L 27/0094* (2013.01);
(Continued)

(58) Field of Classification Search
CPC .. G01N 21/95; G01N 21/9515; H04N 13/254; H04N 13/243; B60M 1/28;
(Continued)

(56) References Cited

U.S. PATENT DOCUMENTS 7,492,448 B2    2/2009  Blair
9,214,016 B2   12/2015  Sacchi et al.
(Continued)

FOREIGN PATENT DOCUMENTS

CN      104567729 A     4/2015
EP        1766326 A1    3/2007
(Continued)

OTHER PUBLICATIONS

Hamey Leonard, G. C., et al, "Pancam: In-Service Inspection of Locomotive Pantographs", Digital Image Computing Techniques and Applications: DICTA 2007; 9th Biennial Conference of the Australian Pattern Recognition Society; Gleneig (I.E. Glenelg), South Australia, XP 002638310, Dec. 3-5, 2007; Proceedings, IEEE Computer Society, Dec. 3, 2007, pp. 493-499.
(Continued)

*Primary Examiner* — Melissa J Koval
*Assistant Examiner* — Courtney G McDonnough
(74) *Attorney, Agent, or Firm* — Pearne & Gordon LLP

(57) ABSTRACT

Method for the video inspection of a pantograph (100) along an overhead contact line, including the steps of: detecting passage of the pantograph (100) in a plurality of monitoring stations (2); in each monitoring station (2), in response to the detection of the passage of the pantograph (100), illuminat-
(Continued)

ing a first overhead zone in which a portion of the pantograph (100) passes; in each monitoring station (2), during the step of illuminating the first overhead zone, acquiring images of the first overhead zone by way of at least one pair of stereo video cameras (5a, 5b); calculating the disparity between the images acquired; reconstructing a three-dimensional model of the portion of the pantograph (100).

5 Claims, 7 Drawing Sheets

(51) Int. Cl.
*B60M 1/28* (2006.01)
*B61L 27/00* (2006.01)
*G01B 11/245* (2006.01)
*H04N 13/254* (2018.01)
*B61K 9/02* (2006.01)
*G01B 11/06* (2006.01)
*H04N 13/239* (2018.01)
*B61L 23/04* (2006.01)
*H04N 13/243* (2018.01)

(52) U.S. Cl.
CPC ............ *G01B 11/06* (2013.01); *G01B 11/245* (2013.01); *G01N 21/9515* (2013.01); *H04N 13/239* (2018.05); *H04N 13/254* (2018.05); *B61L 23/041* (2013.01); *H04N 13/243* (2018.05)

(58) Field of Classification Search
CPC ....... B61K 9/02; B61L 27/0094; B61L 23/04; G01B 11/06; G01B 11/245
USPC ........................................................ 324/217
See application file for complete search history.

(56) References Cited

U.S. PATENT DOCUMENTS

2007/0296949 A1 12/2007 Blair
2010/0253329 A1 10/2010 Arcaini et al.
2012/0274759 A1 11/2012 Kaiser et al.
2013/0195321 A1 8/2013 Sacchi et al.

FOREIGN PATENT DOCUMENTS

IT 1401952 A1 3/2012
JP 2015017921 A1 1/2015
WO 2011035983 A1 3/2011

OTHER PUBLICATIONS

Kin, E., "Pioneer Design in Automatic Pantograph Wear Monitoring", Engineering Integrity, Engineering Integrity Society, United Kingdom, XP 009145699, vol. 19, Mar. 1, 2006, pp. 12-17.

SYSTEM AND METHOD FOR THE VIDEO INSPECTION OF A PANTOGRAPH ALONG AN OVERHEAD CONTACT LINE

TECHNICAL FIELD

The object of the present invention is a system and method for the video inspection of a pantograph along an overhead contact line.

As is known, tractive railway vehicles that pick up current from an overhead contact line usually employ a device known as a "pantograph".

STATE OF THE ART

A pantograph is made up of an articulated system, called a frame, mounted by means of insulators on the roof of the carriage, and a head equipped with contact strips located in direct contact with the wire or wires of the electrical contact line. The contact strips consist of bars made of a conductive material, for example copper, steel, aluminium or carbon.

In this context, reference is made to Y-shaped pantographs comprising two contact strips and two lateral horns. However, the object of the invention is also applicable to other models of pantographs.

The mechanical friction induced when sliding along the contact line causes wear of the contact strips, which, in turn, can cause damage to the locomotive and/or to the electrical line overhead.

To monitor the state of wear of the contact strips so that they can be repaired or replaced before the railway line is damaged, inspection systems have been developed, including both manual and automatic systems, for inspection of the state of wear of the pantographs.

For example, the solution disclosed in the Italian patent No. 1401952 is part of this latter group, and it concerns an automatic diagnostic system for images of a pantograph captured by a plurality of cameras situated in an equal number of image acquisition stations distributed along a railway line. The images acquired by each camera are sent to a remote server that carries out suitable processing procedures and in the presence of damage to the pantograph (e.g. missing or bent horns, misalignment, etc.), it generates automatic alarm signals.

Although it is more reliable than the inspection systems that incorporate optical fibres, the solution described above is not without several problems of its own. In particular, all systems that are based on the use of only one video camera fail to obtain good measurements of the thickness of the contact material on the entire area of the contact strips or to identify and measure possible cracks.

There are also systems available on the market for reconstruction of a three-dimensional model of a pantograph based on the use of video cameras of the laser-scanner type.

Yet, in addition to being very costly, these systems require a complex infrastructure for installation. In fact, to ensure reliable measurements, the video cameras have to be positioned above the moving pantograph. Moreover, they have to be calibrated directly at the installation site. Not least, the reliability of the measurements depends on the speed of the pantograph, which can reach 300 km/h and higher.

For example, document EP 1766326 discloses a solution of this type.

The document WO 2011/035983 discloses a system for monitoring several structural elements, among which the catenary and the contact strips of a pantograph, based on the use of a plurality of video cameras arranged on a portal above the pantograph.

In addition to the problems listed above, the difficulty involved in obtaining a complete model of the pantograph, that is, regarding the contact strips and the lateral horns, should also be noted.

In document JP 2015017921 a pair of stereo video cameras are employed, which are located above the overhead contact line, for acquiring images of the contact strips.

Also document CN 104567729 discloses a system for acquiring images of the catenary and of the contact strips, which is located above the overhead contact line.

The commercial system known as "Pancam" discloses instead the use of two cameras, respectively located on the side and above the overhead contact line.

Document US 2010/253329 discloses a pantograph video inspection system comprising one camera located on a side post with the scope of monitoring the equipment during the transit of the car bearing the pantograph.

Aim of the Invention

In this context, the technical task underlying the present invention is to offer a system and method for the video inspection of a pantograph along an overhead contact line which overcome the above-mentioned drawbacks of the prior art.

In particular, an aim of the present invention is to make available a system and method for the video inspection of a pantograph along an overhead contact line which make it possible to reconstruct a three-dimensional model of the pantograph that is more reliable compared to known solutions and that functions independently of the speed of the locomotive.

Another aim of the present invention is to offer a system and method for the video inspection of a pantograph along an overhead contact line which provide for a complete reconstruction of the pantograph, that is, a reconstruction that includes the contact strips and the lateral horns.

A further aim of the present invention is to offer a system for the video inspection of a pantograph along an overhead contact line, based on a simpler, safer and more economical infrastructure compared to prior-art solutions.

The defined technical task and the specified aims are substantially achieved by a system for the video inspection of a pantograph along an overhead contact line, comprising: a plurality of monitoring stations, each of which comprises detection means for detecting the passage of the pantograph, a first illumination means for illuminating a first overhead zone in which a portion of the pantograph passes, a first acquisition means for acquiring images of the first overhead zone and a local processor; in each one of the monitoring stations, the acquisition means for acquiring images comprises at least one pair of stereo video cameras, the local processor being configured to calculate the disparity between the images acquired by each pair of stereo video cameras.

Preferably, the detection means for detecting the passage of the pantograph comprises a laser telemeter.

Preferably the first illumination means comprises a first panel that has a planar extension and bears a plurality of LED sources. The first panel is situated at a pre-established height with respect to the ground and oriented so as to emit a light beam that floods said first overhead zone.

Preferably, in each monitoring station, the first panel and the pair of stereo video cameras are arranged and oriented in such a manner that the acquired images of the corresponding first overhead zone are frames of an upper portion and an end portion of the pantograph in transit.

Preferably, each monitoring station comprises a second illumination means for illuminating a second overhead zone in which the remaining portion of the pantograph passes, and an additional video camera for acquisition of images of the second overhead zone.

Preferably, the second illumination means comprises a second panel that has a planar extension and bears a plurality of LED sources. The second panel is situated at a pre-established height with respect to the ground and oriented so as to emit a light beam that floods the second overhead zone.

Preferably, in each monitoring station, the additional video camera is arranged and oriented in such a manner that the images acquired from the corresponding second overhead zone are frames of the remaining end portion of the pantograph in transit.

Preferably, each monitoring station comprises a first post and a second post situated on opposite sides with respect to the overhead contact line. In particular, the first post bears the laser telemeter, the first panel and the pair of stereo video cameras. The second post bears the second panel and the additional video camera.

The defined technical task and the specified aims are substantially achieved by a method for the video inspection of a pantograph along an overhead contact line, comprising the steps of:
- detecting passage of the pantograph in a plurality of monitoring stations;
- in each monitoring station, in response to the detection of the passage of the pantograph, illuminating a first overhead zone in which a portion of the pantograph passes;
- in each monitoring station, during the step of illuminating the first overhead zone, acquiring images of the first overhead zone;
- processing the images acquired from each monitoring station.

Originally, in each first overhead zone, the images are acquired by at least one pair of stereo video cameras and the step of processing the acquired images comprises a sub-step of calculating the disparity and a sub-step of reconstructing the three-dimensional model of the portion of the pantograph.

Preferably, in each monitoring station, in response to the detection of the passage of the pantograph, a second overhead zone is illuminated in which the remaining portion of the pantograph passes.

During this illumination process, images of the second overhead zone are acquired. In this manner, the step of processing the images also uses the images acquired in the corresponding second overhead zone so as to complete the three-dimensional model of the pantograph.

Advantageously, the reconstructed model of the pantograph for each monitoring station is compared with an ideal model of the pantograph so as to obtain information on the state of wear of the pantograph.

BRIEF DESCRIPTION OF THE DRAWINGS

Further characteristics and advantages of the present invention will become more apparent from the approximate and thus non-limiting description of a preferred, but not exclusive, embodiment of a system and method for the video inspection of a pantograph along an overhead contact line, as illustrated in the accompanying drawings, of which:

FIG. 8 is a perspective view of a part (first post) of the video inspection system of the FIG. 2, according to an additional embodiment.

DETAILED DESCRIPTION OF PREFERRED EMBODIMENTS OF THE INVENTION

Figure 1:
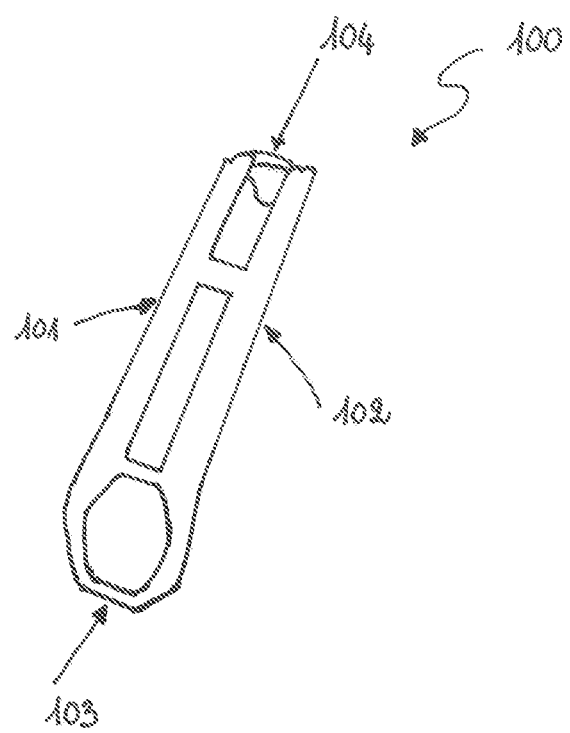
FIG. 1 is a schematic side view of a Y-shaped type of pantograph, seen from above.
Figure 2:
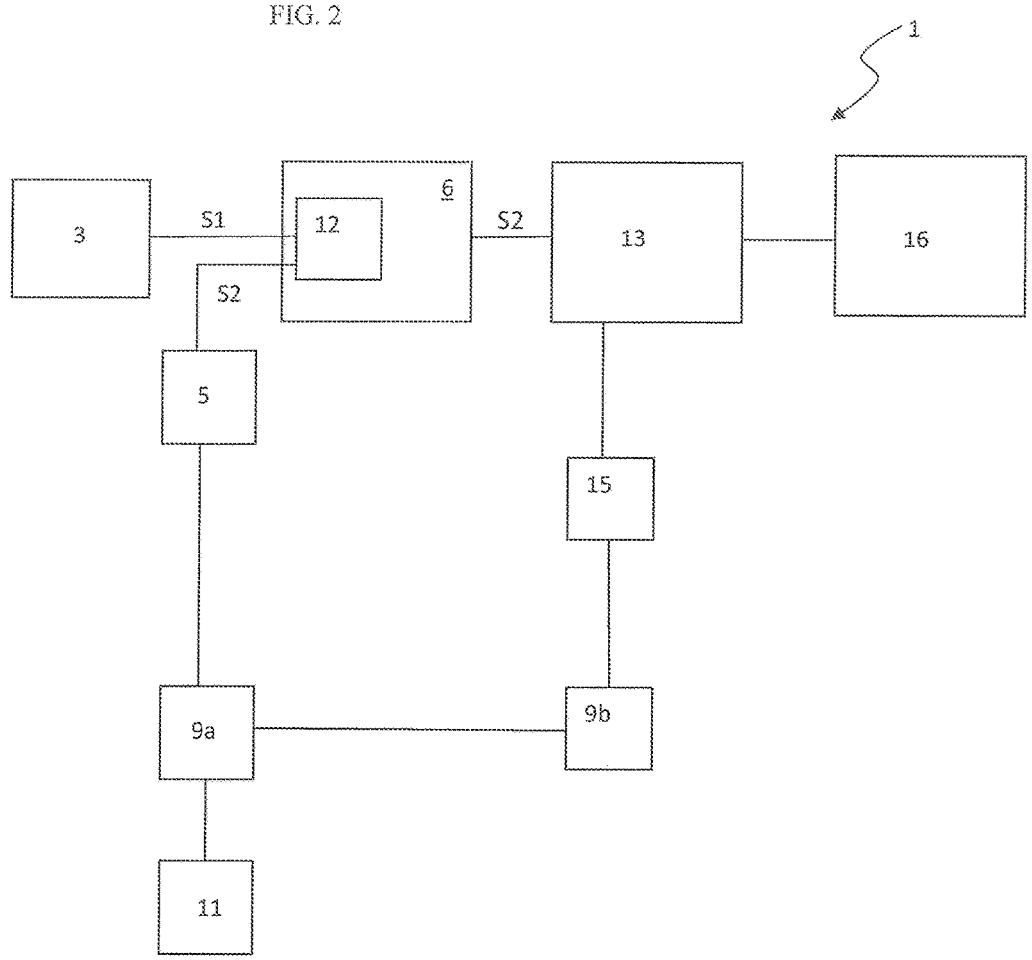
FIG. 2 is a simplified block diagram of a video inspection system according to the present invention.

With reference to the figures, number 1 indicates a system for the video inspection of a pantograph 100 along an overhead contact line, for example installed on a locomotive.

In the embodiments described and illustrated herein, the pantograph 100 is a Y-shaped pantograph comprising two contact strips 101, 102 in contact with the overhead line and two lateral horns 103, 104.

The system 1 comprises a plurality of monitoring stations 2 that are distributed along the overhead contact line.

Each monitoring station 2 comprises:
- detection means 3 for detecting passage of the pantograph 100;
- a first illumination means 4 for illuminating a first overhead zone in which a portion of the pantograph 100 passes;
- a first acquisition means 5 for acquiring images of the first overhead zone.

Originally, the first acquisition means 5 for acquiring images comprises at least one pair of stereo video cameras 5a, 5b. Preferably, the two stereo video cameras 5a, 5b are matrix video cameras and they have a resolution of 2-20 M pixels.

Each one of the stereo video cameras 5a, 5b has a sensor of the CMOS type (acronym for "Complementary Metal Oxide Semiconductor") or CCD type (acronym for "Charge Coupled Device").

Preferably, the detection means 3 for detecting passage of the pantograph 100 comprises a laser telemeter 3 of a known type.

Preferably, the first illumination means 4 for illuminating the first overhead zone is realized with LED technology.

For example, the first illumination means 4 comprises a first panel 6 that has a planar extension and bears a plurality of LED sources 7. Preferably, each LED source 7 can be oriented along two axes (in optics, this is known as "pan/tilt" rotation).

In particular, the first panel 6 is situated at a pre-established height with respect to the ground T and oriented so as to emit a light beam that floods said first overhead zone.

In the embodiment described and illustrated herein, the portion of the pantograph 100 that passes and is illuminated and acquired in the first overhead zone of each monitoring station 2 corresponds to the upper central portion (two contact strips 101, 102) and to an end portion (one of the horns 103, 104).

Preferably, in each monitoring station 2, the first panel 6 and the pair of stereo video cameras 5a, 5b are arranged and oriented in such a manner that the acquired images of the corresponding first overhead zone are frames of the two contact strips 101, 102 and one of the horns 103, 104 of the pantograph 100 in transit, seen from above.

Preferably, the two stereo video cameras 5a, 5b are positioned according to a horizontal baseline. As is known, the term "baseline" indicates the distance between the optical axes of a pair of stereo video cameras. In this case, the baseline is comprised between 10 and 50 cm.

Figure 6:
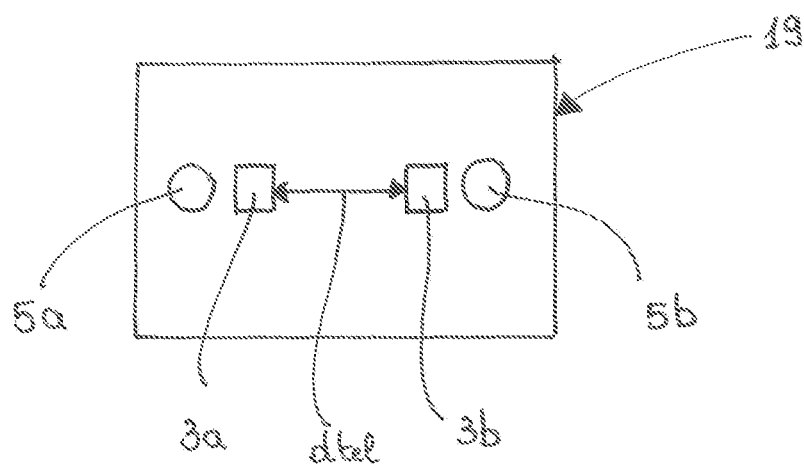
FIG. 6 illustrates the arrangement of the video cameras and the telemeters of the video inspection system of FIG. 2, in a variant embodiment.
Figure 7:
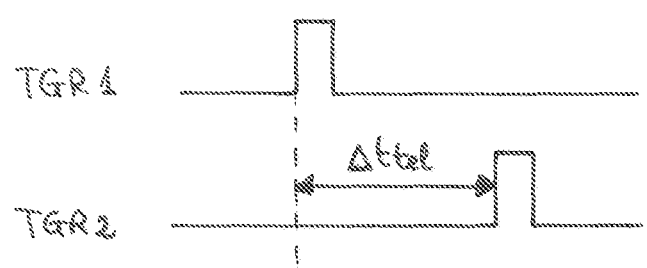
FIG. 7 illustrates some characteristic signals of the variant embodiment of FIG. 6.
Figure 9:
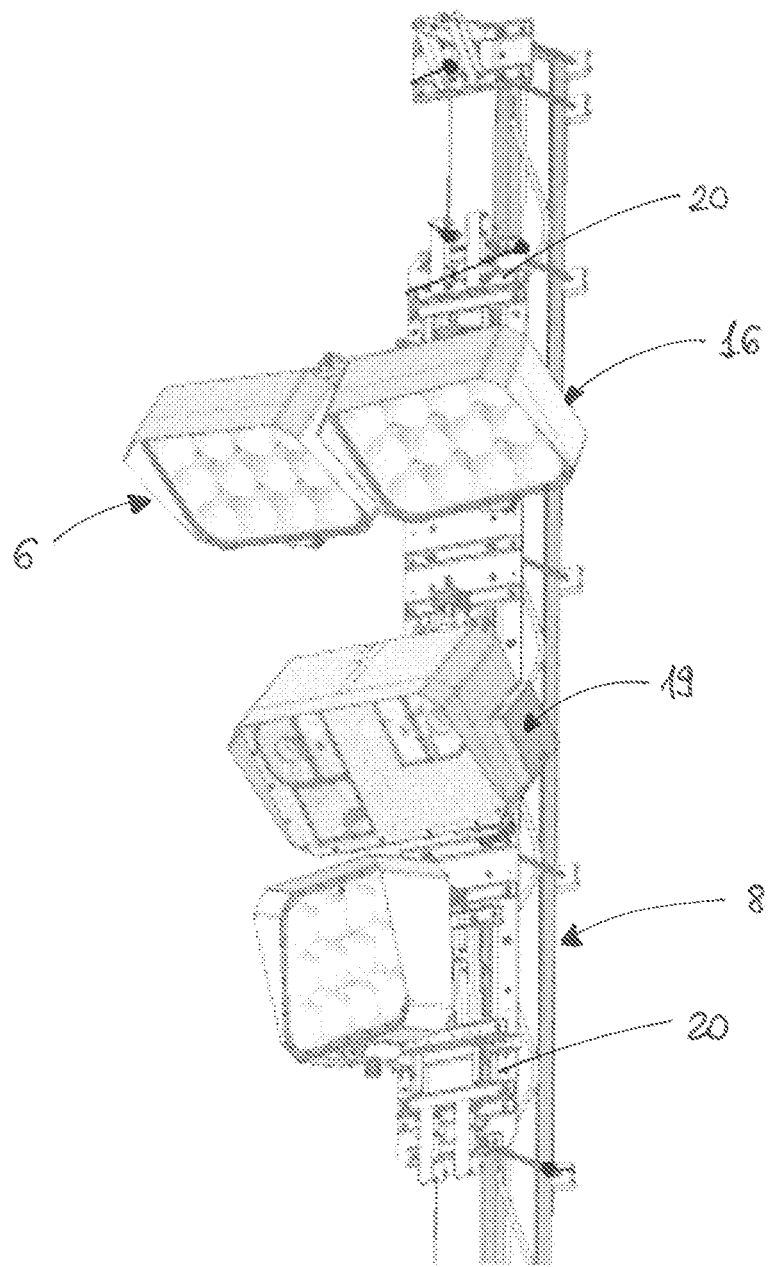

More preferably, the detection means 3 for detecting passage of the pantograph 100 comprises two laser telemeters 3a, 3b of a known type arranged according to a horizontal baseline at a pre-established distance $d_{tel}$ from each other. The two laser telemeters 3a, 3b also lie on the same horizontal axis as the two stereo video cameras 5a, 5b and they are interposed between these video cameras (see FIG. 6).

In the embodiment described and illustrated herein, a first post 8 is located in each monitoring station 2 and it bears the laser telemeters 3, the first panel 6 and the pair of stereo video cameras 5a, 5b.

Preferably, each monitoring station 2 comprises a first local or master processor 9a, which is configured to calculate the disparity between the images acquired by each pair of stereo video cameras 5a, 5b.

Preferably, the disparity is calculated using algorithms of a known type. Given that it is not possible to obtain a perfect horizontal alignment of the pair of stereo video cameras 5a, 5b, the first local processor 9a is preferably also configured to perform rectification of the acquired images. In particular, rectification is carried out by means of known algorithms. Lastly, given that the lenses of the stereo video cameras 5a, 5b introduce distortions, the first local processor 9a is preferably also configured to perform distortion correction of the acquired images (this too by means of known algorithms).

Preferably, a data storage module (unillustrated) is also present in each monitoring station 2.

Meteorological data such as air temperature and wind direction and speed detected by a weather station (of a known type) are among the significant data stored in the storage module.

Moreover, it is possible to record data concerning:
diagnostics relating to the operation of the video cameras, LED sources and batteries;
position of the overhead contact line of the pantograph;
direction of travel and speed of the railway vehicle;
identification of the vehicle.

The system 1 further comprises a central processor 11 that communicates with the monitoring stations 2 by means of a cabled or wireless connection. Preferably, the central processor 11 is a remote server adapted to receive data (among which the disparity map) from the local master processors 9a of the monitoring stations 2, which function as clients.

Advantageously, each monitoring station 2 comprises:
a second illumination means 14 for illuminating a second overhead zone in which the remaining portion of the pantograph 100 passes;
an additional video camera 15 for acquiring images of the second overhead zone.

Preferably, the additional video camera 15 is a matrix video camera and it has a resolution of 2-16 M pixels.

Preferably, the second illumination means 14 for illuminating the second overhead zone is realized with LED technology.

For example, the second illumination means 14 comprises a second panel 16 that has a planar extension and bears a plurality of LED sources 17. Preferably, each LED source 17 can be oriented along two axes ("pan/tilt" axes).

In particular, the second panel 16 is situated at a pre-established height with respect to the ground T and oriented so as to emit a light beam that floods the second overhead zone.

In the embodiment described and illustrated herein, the remaining portion of the pantograph 100 that passes and is illuminated and acquired in the second overhead zone corresponds to the end portion that is not covered by the first overhead zone (that is, the other one of the two horns 103, 104).

Preferably, in each monitoring station 2, the second panel 16 and the additional video camera 15 are arranged and oriented in such a manner that the acquired images of the corresponding second overhead zone are frames not yet acquired of the horn 103, 104 of the pantograph 100 in transit, seen from above.

In the embodiment described and illustrated herein, a second post 18 is located in each monitoring station 2 and it bears the second panel 16, the additional video camera 15 and a second local processor 9b that communicates with the first local processor 9a. In particular, the first local processor 9a functions as the "master" and the second local processor 9b as the "slave". Communication between the two local processors 9a, 9b is preferably wireless.

In particular, the first post 8 and the second post 18 are located on opposite sides with respect to the overhead contact line.

The system for video inspection 1 described thus far is adapted to monitor the pantograph 100 for a single-track line.

In the case of a double-track line, the conditions of two pantographs 100 must be monitored, one pantograph 100 being associated with the locomotive of the outbound track Ba and one associated with the locomotive of the inbound track Br.

The structure of the system 1 for a double-track line is similar to that for a single-track line, with necessary duplication of some elements.

In particular, each monitoring station 2 of the outbound track Ba proves to be "distributed" on the first post 8 and on the second post 18 as follows:
the first post 8, which is located to the side of the outbound track Ba, supports the laser telemeter 3 (or the two laser telemeters 3a, 3b), the first panel 6, the pair of stereo video cameras 5a, 5b and the first local processor 9a;
the second post 18, which is located to the side of the inbound track Br, supports the second panel 16, the additional video camera 15 and the second local processor 9b.

In a similar manner, each monitoring station 2 of the inbound track Br is distributed on the same two posts 8, 18, but with reversed functions. In fact, in this case it is the second post 18 that bears the laser telemeter 3 (or the two laser telemeters 3a, 3b), the first panel 6, the pair of stereo video cameras 5a, 5b and the first local processor 9a for the inbound track Br. The first post 8 instead bears the second panel 16, the additional video camera 15 and the second local processor 9b.

Preferably, the first post 8 comprises a housing box 19 for the pair of stereo video cameras 5a, 5b that are operatively active on the pantograph 100 for the outbound track Ba and for the additional video camera 15 that is operatively active on the pantograph 100 for the inbound track Br.

The laser telemeter 3 (or the two laser telemeters 3a, 3b) that is operatively active on the pantograph 100 for the outbound track Ba is also arranged in this housing box 19.

The second post 18 comprises a housing box 29 for the pair of stereo video cameras 5a, 5b that are operatively active on the pantograph 100 for the inbound track Br and for the additional video camera 15 that is operatively active on the pantograph 100 for the outbound track Ba.

The laser telemeter 3 (or the two laser telemeters 3a, 3b) that is operatively active on the pantograph 100 for the inbound track Br is also arranged in this housing box 29.

Figure 3:
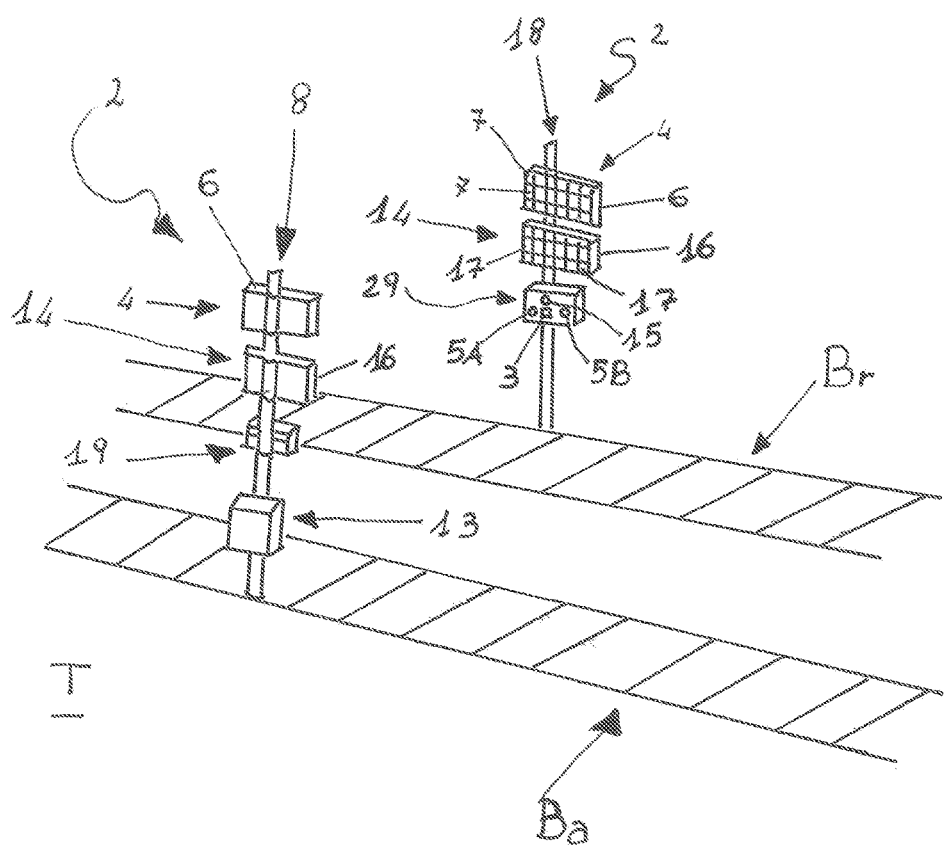
FIG. 3 schematically illustrates part of the video inspection system of FIG. 2, applied to a double-track line.
Figure 4:
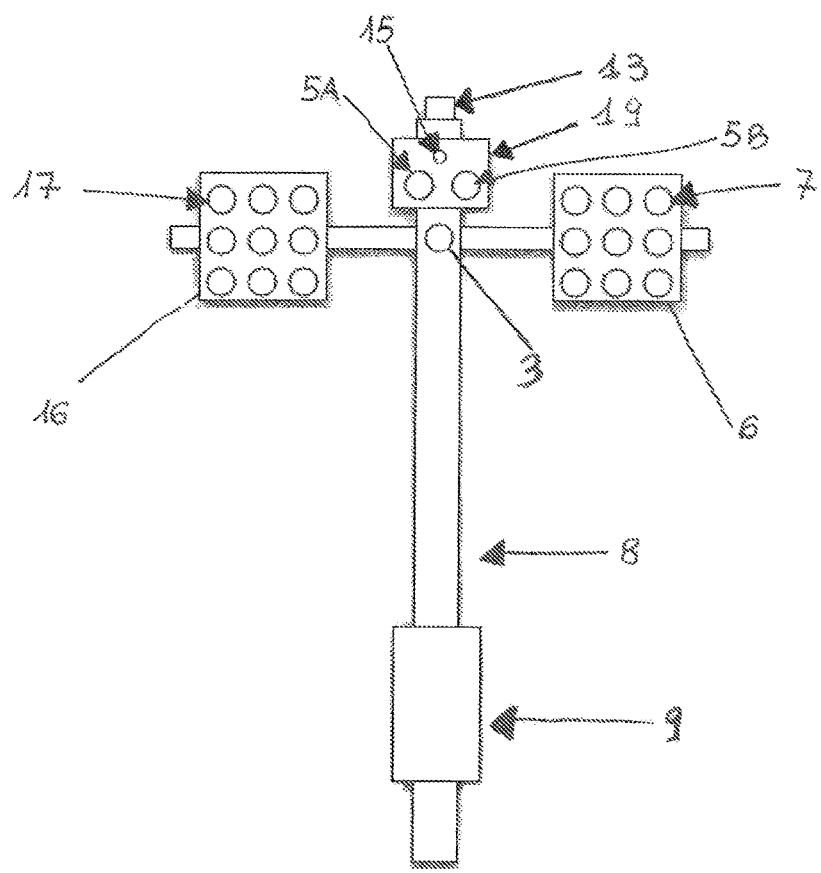
FIGS. 4 and 5 illustrate a part (first post) of the video inspection system of FIG. 2, according to a different embodiment, in a front and a side view, respectively.
Figure 5:
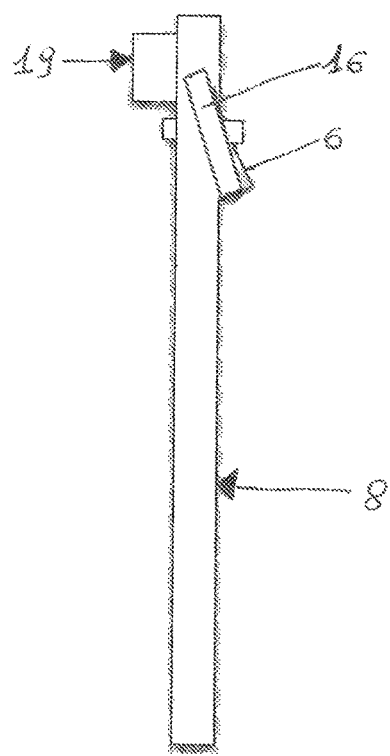

In each post 8, 18, the panels 6, 16 can be arranged at different heights (as in FIG. 3) or at the same height (as in FIGS. 4 and 5). In the case in which the panels 6, 16 are at the same height, they are tilted at different angles, with respect to the ground, (as shown in FIG. 5) because they need to illuminate a first overhead zone of passage of the pantograph for the nearest track and a second overhead zone of passage of the pantograph for the furthest track, respectively.

Instead of employing four panels, one (unillustrated) variant embodiment employs:

only one panel on the first post 8, said panel comprising several LED sources that can be oriented so as to illuminate the first overhead zone in which the upper and external end portion of the pantograph 100 associated with the outbound track Ba passes, and several LED sources that can be oriented so as to illuminate the second overhead zone in which an internal end portion of the pantograph 100 associated with the inbound track Br passes;

only one panel on the second post 18, said panel comprising several LED sources that can be oriented so as to illuminate the first overhead zone in which the upper and external end portion of the pantograph 100 associated with the inbound track Br passes, and several LED sources that can be oriented so as to illuminate the second overhead zone in which the internal end portion of the pantograph 100 associated with the outbound track Ba passes.

Preferably, the installation of the various components (housing boxes 19, 29, panels 6, 16, etc.) on the posts 8, 18 is possible owing to a supporting structure 20 slidingly mounted on each post 8, 18 by means of a pulley mechanism. In this manner, installation and maintenance procedures are made easier.

For example, an installation of this type, with an additional illumination panel 26, is shown in FIG. 8.

The wireless communication module 13 and the local processors 9a, 9b are instead preferably located at the base of each post 8, 18 to facilitate access to them.

Alternative embodiments provide for the use of supporting structures differing from the posts 8, 18, but in any case, preferably located to the side of the tracks Ba, Br.

The method for the video inspection of a pantograph along an overhead contact line is described herein below.

For the sake of simplicity, reference is made here to a single-track line on which a locomotive with the relative pantograph 100 passes.

In each monitoring station 2, the laser telemeter 3 positioned on the first post 8 detects the passage of the pantograph 100 and generates an activation signal S1 for a control unit 12 controlling the LED sources 7 of the first panel 6 so as to activate these sources 7 and thus illuminate the first overhead zone.

The control unit 12 controlling the LED sources 7, in turn, sends a synchronization signal S2 to the pair of stereo video cameras 5a, 5b (previously calibrated according to known techniques), which acquire images of the first overhead zone.

In particular, the acquired images are of the contact strips 101, 102 and the external horn 103 (the one closest to the first post 8) of the pantograph 100 in transit, seen from above.

The first local processor 9a calculates the disparity between the images acquired and sends it to the central processor 11.

The synchronization signal S2 is also sent to the LED sources 17 of the second panel 16 and to the additional video camera 15, all of which are situated on the second post 18. In other words, the first panel 6 performs the function of the "master", and the second panel 16 performs the function of the "slave". In a variant embodiment, the function of the "master" is performed directly by the pair of stereo video cameras 5a, 5b. The synchronization signal S2 is sent from the first post 8 to the second post 18 by means of a wireless communication module 13 located on the first post 8. In a variant embodiment, the communication module 13 is incorporated in the first panel 6. In response to the synchronization signal S2, the LED sources 17 of the second panel 16 switch on and the additional video camera 15 acquires images of the second overhead zone.

In particular, the acquired images are of the internal horn 104 (the one closest to the second post 18) of the pantograph 100 in transit, seen from above.

These images are also sent to the central processor 11, which is configured to reconstruct the three-dimensional model of the pantograph 100.

The central processor 11 is further configured to compare the reconstructed model of the pantograph 100 for each monitoring station 2 with an ideal model of the pantograph 100 so as to obtain information on the state of wear of the pantograph 100.

Moreover, the stereoscopic view from the two video cameras 5a, 5b makes it possible to take absolute spatial measurements and not only relative measurements.

Therefore, the central processor 11 is configured to process the reconstructed model and to obtain dimensions of possible cracks, areas affected by wear, etc., without the need for comparison with the ideal model.

Preferably, for each monitoring station 2, the first overhead zone to be illuminated is selected so as to include a slice of the overhead contact line as well. In this manner, information concerning the position of this slice during passage of the pantograph 100 is obtained from the disparity calculation performed by the local processor 9a.

Preferably, the central processor 11 is also configured to compare the position of the slice of the overhead contact line during passage of the pantograph 100 and the position of this slice in the absence of the pantograph 100, that is, at rest.

The embodiment that employs two laser telemeters 3a, 3b interposed between the stereo video cameras 5a, 5b makes it possible to detect the passage of the pantograph 100 and to calculate the speed thereof (and therefore also the speed of the train).

In particular, in each monitoring station 2, one of the two telemeters—which we shall call the "first telemeter 3a"—positioned on the first post 8 is the first to detect the passage of the pantograph 100 and it generates a first trigger signal TGR1. The other telemeter—which we shall call the "second telemeter 3b"—positioned on the same post 8 detects the passage of the pantograph 100 subsequently, generating a second trigger signal TGR2 which is delayed with respect to the first trigger signal TGR1. The pre-established distance $d_{tel}$ between the two telemeters 3a, 3b is known (this is a design constraint) and the time delay $\Delta t_{tel}$ between the first and the second trigger signals TGR1, TGR2 is measurable. Therefore, the speed V of the pantograph 100 (and of the train) can be obtained using the following relation:

$$V(km/h)=d_{tel}(mm)/\Delta t_{tel}(ms)*3.6.$$

Having calculated the speed V of the pantograph 100, the activation signal S1 for activating the LED sources 7 is then generated and the video cameras 5a, 5b are synchronized as explained hereinabove. The advantage of using the two telemeters 3a, 3b lies in the fact that knowing of the speed V of the pantograph 100 makes it possible to calculate the exact instant in which the activation signal for activating the LED sources 7 and video cameras 5a, 5b should be generated, so that the portions of the pantograph 100 acquired in the first overhead zone always fall within the same area of the image, regardless of the model of the pantograph 100. The characteristics of a system and method for the video inspection of a pantograph along an overhead contact line, according to the present invention, prove to be clear from the description provided, as do the advantages thereof.

In particular, the use of a pair of stereo video cameras for each monitoring station makes it possible to reconstruct a very precise three-dimensional model of the pantograph, which is not compromised by the speed of the locomotive (which can reach a speed of up to 300 km/h for example).

By comparing the three-dimensional model thus reconstructed with the ideal model of the pantograph, it is therefore possible to obtain reliable information concerning the actual conditions of the pantograph (areas affected by wear, cracks, chipping, defects, etc.) and thus plan maintenance or replacement procedures.

Moreover, the use of an additional video camera makes it possible to complete the reconstructed model of the pantograph owing to the acquisition of images of the furthermost horn.

The proposed method also enables monitoring of the pressure of the pantograph on the overhead line (wire), thus avoiding the use of additional instruments on board the line.

Furthermore, unlike the solutions that employ sensors of the "laser-scanner" type, which require placement on frames above the tracks, in this case the pair of stereo video cameras and the LED sources can be positioned in safer sites alongside the line.

For example, they can be positioned on posts or other lateral supports without affecting the quality of the acquired images.

Furthermore, infrastructures already existing along the railway lines can be used, with obvious advantages in terms of the space occupied, efficiency and costs.

This also makes it possible to simplify installation and maintenance of the video inspection system.

Moreover, the same supporting infrastructure can be used for the system applied to single-track lines and for the system applied to double-track lines.

The use of LED illumination technology satisfies the needs relating to duration and reliability for these types of systems. In addition, the redundancy of the LED sources provides for continuity of use of the system even in the case of failure of some sources.

The invention claimed is:

1. System for the video inspection (1) of a pantograph (100) comprising contact strips (101, 102) at the upper central portion and horns (103, 104) at the end portions along an overhead contact line in a railway track, comprising:
    a plurality of monitoring stations (2), each of which comprises:
        detection means (3) for detecting passage of the pantograph (100) comprising at least one laser telemeter;
        a first illumination means (4) for illuminating a first overhead zone in which a portion of the pantograph (100) passes, said first illumination means (4) comprising a first panel (6) that has a planar extension and bears a plurality of LED sources (7);
        at least one pair of stereo video cameras (5a, 5b) for acquiring images of said first overhead zone;
        a first local processor (9a) configured to calculate the disparity between the images acquired by each pair of stereo video cameras (5a, 5b);
        a second illumination means (14) for illuminating a second overhead zone in which the remaining portion of the pantograph (100) passes, said second illumination means (14) comprising a second panel (16) that has a planar extension and bears a plurality of LED sources (17);
        an additional video camera (15) for acquisition of images of said second overhead zone;
        a first and a second supporting structures (8, 18) situated to the side of the track and on opposite sides with respect to said overhead contact line, wherein the first supporting structure (8) bears said laser telemeter (3), said first panel (6) and said stereo video cameras (5a, 5b), while the second supporting structure (18) bears said second panel (16) and said additional video camera (15), said stereo video cameras (5a, 5b) and said first panel (6) being arranged and oriented in such a manner that the acquired images of the first overhead zone are frames of the upper central portion and an end portion of the pantograph (100) seen from above in transit, said additional video camera (15) being arranged and oriented in such a manner that the images acquired from the corresponding second overhead zone are frames of the remaining end portion of the pantograph (100) seen from above in transit;
    a central processor (11) communicating with the monitoring stations (2) by means of a cabled or wireless connection, said central processor (11) being configured to receive the computation of the disparity from the first local processor (9a) of each monitoring station (2) and the images acquired from the additional video camera (15), to reconstruct the three-dimensional model of the pantograph (100) and to compare said reconstructed model with an ideal model of the pantograph (100) so as to obtain information on the state of wear of the pantograph (100) itself.

2. System for video inspection (1) according to claim 1, wherein said stereo video cameras (5a, 5b) are arranged according to a horizontal baseline.

3. System for video inspection (1) according to claim 2, wherein said detection means (3) for detecting passage of the pantograph comprises two laser telemeters (3a, 3b) interposed between said stereo video cameras (5a, 5b) and arranged according to the same horizontal baseline.

4. System for video inspection (1) according to claim 1, wherein said first panel (6) is situated at a pre-established height with respect to the ground (T) and is oriented so as to emit a light beam that floods said first overhead zone.

5. System for video inspection (1) according to claim 1, wherein said second panel (16) is situated at a pre-established height with respect to the ground (T) and is oriented so as to emit a light beam that floods said second overhead zone.

* * * * *